United States Patent [19]

Christensen

[11] 4,315,934
[45] Feb. 16, 1982

[54] ORGANIC COMPOUNDS

[75] Inventor: Anne V. Christensen, Farum, Denmark

[73] Assignee: Sandoz Ltd., Basel, Switzerland

[21] Appl. No.: 188,686

[22] Filed: Sep. 19, 1980

[30] Foreign Application Priority Data

Sep. 24, 1979 [GB] United Kingdom ............... 32990/79

[51] Int. Cl.³ .......................................... A61K 31/435
[52] U.S. Cl. .................................................... 424/256
[58] Field of Search ......................................... 424/256

[56] References Cited

FOREIGN PATENT DOCUMENTS 338 1/1979 European Pat. Off. .

OTHER PUBLICATIONS

Br. J. Pharmac. (1979), 67, 103–107.
European J. of Pharmacology, 48 (1978), 459–462.
Neuropharmacology 1977, 16, 149–150.
Pharmacological Research Comm., vol. 12, No. 3 (1980), 239–247.
Neuropharmacology, vol. 19, 1980, 715–722.
European J. of Pharmacology, 61 (1980) (11-5-79) 225–230.

*Primary Examiner*—Stanley J. Friedman
*Attorney, Agent, or Firm*—Gerald D. Sharkin; Robert S. Honor; Timothy G. Rothwell

[57] ABSTRACT

The analgesic use of compounds of formula I

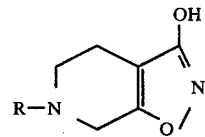

wherein R is hydrogen, acetyl or a group of formula II

R'—O—CO—  II wherein R' is alkyl ($C_{1-8}$); phenyl; phenyl substituted in the 4-position with halogen, alkoxy($C_{1-4}$) or alkyl($C_{1-4}$); phenylalkyl; or phenylalkyl in which the phenyl group is substituted in the 4-position with halogen, alkoxy($C_{1-4}$) or alkyl ($C_{1-4}$).

5 Claims, No Drawings

ORGANIC COMPOUNDS

The present invention relates to a novel pharmaceutical use for the compounds of formula I

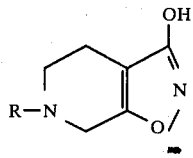

wherein R is hydrogen, acetyl or a group of formula II

R'—O—CO—    II wherein R' is alkyl ($C_{1-8}$); phenyl; phenyl substituted in the 4-position with halogen, alkoxy ($C_{1-4}$) or alkyl ($C_{1-4}$); phenylalkyl; or phenylalkyl in which the phenyl group is substituted in the 4-position with halogen, alkoxy ($C_{1-4}$) or alkyl ($C_{1-4}$).

The compounds of formula I may also exist as zwitterions of formula Ia and tautomers of formula Ib;

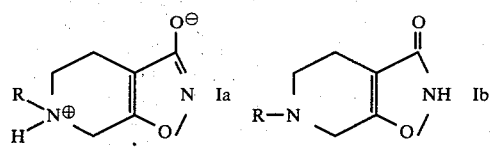

For the sake of convenience formula I as used herein is to be understood as including both the zwitterion and tautomeric forms of formula Ia and Ib as well as mixtures thereof and references to formula I as well as to individual compounds of formula I throughout the specification and claims are to be construed accordingly.

The compounds of formula I as well as processes for their production are known e.g. from European Patent Application No. 78 100 191.2 filed June 19th, 1978 and published Jan. 24th, 1979 (publication No. 338).

These compounds are known to possess γ-aminobutyric acid (GABA) related activity and are indicated for use for treating GABA system malfunction-related diseases, e.g. neurological and psychiatrical disorders such as epilepsy, parkinsonism, schizophrenia, Huntington's chorea, diseases involving malfunction of the pituitary hormones, and cerebral arteriosclerosis.

It has now surprisingly been found that the compounds of formula I also exhibit analgesic activity as may be indicated in standard animal tests, e.g. as hereinafter described and in clinical trials. The compounds of formula I are therefore useful in alleviating pain of varying aetiology.

The present invention accordingly provides a method of alleviating pain in a subject in need of such treatment, which method comprises administering to said subject an analgesically effective amount of a compound of formula I as hereinbefore defined.

The preferred compound for use in accordance with the method of the invention is the compound of formula I wherein R is hydrogen, namely 4,5,6,7-tetrahydroisoxazolo [5,4-c]pyridin-3-ol, hereinafter referred to as THIP.

The compounds of formula I when not in zwitterion form may be administered in free form or in the form of their pharmaceutically acceptable acid addition salts or pharmaceutically acceptable salts with bases. Such salt forms are also known and include for example the hydrochloride and the metal salts, e.g. the sodium salt.

The activity of such pharmaceutically acceptable salt forms will generally be of the same order as that of the respective free compound form. Though the use of the compounds in free form is generally preferred, the use of pharmaceutically acceptable salt forms is also to be understood as falling within the purview of the present invention.

As used herein all amounts for the formula I compounds recited refer to the amount of the free form. The same applies to weight ratios.

The analgesic activity of the compounds of formula I, e.g. THIP, may be demonstrated in standard animal tests, for example in accordance with the following methods.

(a) Phenyl-p-benzoquinone-induced writhing test in the mouse:

The method employed is based on those described by Siegmund et al. (1975) and Emelz and Shanaman (1967). The test-substance is administered orally at a pre-determined dosage to female mice (12–18g) starved overnight, but allowed access to water. 20 minutes later each mouse receives 2 mg/kg phenyl-p-benzoquinone administered i.p. Immediately afterwards the mice are placed in an environment maintained at 34° C. After a further 5 minutes the mice are observed and the number of "writhes" performed over the course of the next 5 minutes counted and recorded. Five mice are observed at any one time and are placed in three separate cages (2 mice each in 2 cages and the fifth in a third cage) to facilitate observation. Each test substance is administered at 3 to 4 different doses and 5 to 15 mice are employed per dose. The $ED_{50}$ is estimated according to the method of Litchfield and Wilcoxon [J.Pharm.Exp.Ther. 96, 98 (1949)] and is taken as that dose which reduces the total number of abdominal contractions ("writhes") compared with untreated controls by 50%. In the above test the compound THIP was for example found to be active at doses of from about 1 to about 10 mg/kg p.o.. The $ED_{50}$ for THIP was found to be 1.8 mg/kg p.o..

b. Hot plate test in the mouse:

The method employed is based on those described by Woolfe and MacDonald (1944) and Eddy et al. (1953). Female or male mice (16–25 g), starved overnight but allowed access to water are placed in turn on a copper plate maintained at 56° C. by means of a waterbath. The time in seconds taken by each mouse to raise and lick its forepaws is recorded and the test repeated four times for each mouse, the testing times being 15 minutes apart. Mice whose mean reaction time for the 4 trials is longer than 10 seconds or whose reaction time varies by more than 100% are discarded.

The test substance is administered at varying doses either s.c. or orally to the remaining mice and the above procedure repeated, the mice being rested after periods of 30, 60 and 90 minutes.

An increase in the post-treatment reaction time of 75% over the mean pre-treatment reaction time in the same animal is taken to be indicative of an analgesic effect. The number of mice exhibiting analgesia after each treatment is recorded. 3 to 5 doses are used per test substance for each route of administration and from 6 to 10 animals are used per dose. The $ED_{50}$ (95% confidence limits) after 90 minutes is estimated according to the method of Litchfield and Wilcoxon [J.Pharm.Exp.Ther. 96, 98 (1949)] and is taken as that dose producing analgesia in 50% of the mice.

In the above test the compound THIP was found to be active at doses from about 0.1 to about 2.5 mg/kg s.c. and 1.0 to 10 mg/kg p.o. The $ED_{50}$ for THIP was found to be 0.74 mg/kg s.c. and 3.7 mg/kg p.o.

(c) Shock titration test in the rhesus monkey:

The method employed is based on those described by Boren and Malis (1961), Weitzman and Ross (1962) and Weiss and Laties (1961, 1964), and permits continuous measurement of the tolerated pain threshold independent of any decision by the experimenter.

Trained rhesus monkeys are subjected via platinum electrodes clipped to their ears to electrical shocks increasing stepwise and geometrically in intensity (factor 1.21) from 0.21 to 8.25 m A. Each animal is allowed access to a lever which on depression reduces the strength of the next shock by one step. The monkeys are thus able to titrate their own threshold above which they will not tolerate shock.

The tolerated stimulus intensity is determined 60 and 30 minutes before and 35, 60, 90, 135, 200 and 300 minutes after oral or sub-cutaneous administration of the test substance at the test dose.

The experiment is interpreted on the basis of positive reaction (i.e. pressing of the lever between shocks) or negative reaction (i.e. tolerance of the shock applied). For the calculation of the results the lesser of the two totals for positive and negative reaction is taken, and the calculation is based upon the "up and down" method of Dixon and Massey (1975).

2 to 5 doses are employed for each test substance and for each route of administration and from 1 to 16 monkeys are investigated per dose. The significance of the change in the tolerated stimulus threshold at each observation time compared with the pre-treatment values is evaluated employing variance analysis and the minimal effective dose (MED) for the test substance determined.

In the above test the compound THIP was found to be effective at doses of from about 5.6 to about 10 mg/kg s.c and from about 18 to about 50 mg/kg p.o. The MED for THIP was found to be 5.6 mg/kg s.c. and 18 mg/kg p.o.

The compound THIP is physiologically well tolerated, for example over periods of 14 days administered at a dosage of 60 mg/kg/day p.o. in rats and at a dosage of 20 mg/kg/day p.o. in dogs and baboons. The $LD_{50}$ for THIP is 70 mg/kg i.v. and 195 mg/kg p.o. in the mouse. The tolerability of other compounds of formula I is of the same order as that of THIP.

The amount of compound administered in practicing the method of the invention will of course vary according to e.g. the particular compound employed, the mode of administration, the condition to be treated and the therapy desired.

In general satisfactory results are obtained using the compounds of formula I, e.g. THIP, at a daily dose of from about 0.1 to about 20 mg/kg. Conveniently the compound is presented in unit dosage form administered 2 to 4 times a day or in sustained release form. For the larger mammal a suitable oral daily dosage is from about 10 to about 200 mg preferably from about 15 to about 100 mg. most preferably from about 20 to about 50 mg and a suitable unit dosage form contains from about 2 to about 100 mg, preferably from about 5 to about 25 mg of for example the compound THIP in association with a pharmaceutical carrier or diluent.

Pharmaceutical compositions for use in the method of the invention may be prepared in accordance with standard techniques for example by admixture of the active ingredient with conventional pharmaceutically acceptable diluents or carriers and optionally other excipients. Suitable forms for administration include tablets, capsules and injectable solutions. Solid forms, in particular unit dosage forms, suitable for oral administration are preferred.

In addition to the foregoing the present invention also provides in a further aspect a pack containing a pharmaceutical composition comprising a compound of formula I as active ingredient, together with instructions for the administration of said compound as an analgesic.

The following examples illustrate compositions for use in accordance with the method of the invention.

EXAMPLE

Production of pharmaceutical compositions

Tablets may contain the active agent in admixture with conventional pharmaceutically acceptable excipients, e.g. inert diluents, such as calcium carbonate, sodium carbonate, lactose and talc, granulating and disintegrating agents, e.g. starch and alginic acid, flavouring, colouring and sweetening agents, binding agents, e.g. starch, gelatin and acacia, and lubricating agents, e.g. magnesium stearate, stearic acid and talc. The tablets may be uncoated or coated by known techniques to delay disintegration and absorption in the gastrointestinal tract and thereby provide a sustained action over a long period.

For the manufacture of tablets, the compouds of formula I can be mixed with lactose and granulated with water and 0.5% polyvinylpyrrolidone or 1% gelatine solution. The dried granulate is compressed into tablets in the presence of about 5% of corn starch and 0.1% of magnesium stearate. In this way, there are obtained, e.g. tablets of the following compositions:

| Ingredients | 5 mg Tablet | 25 mg Tablet |
| --- | --- | --- |
| Compound of formula I e.g. THIP | 5.0 mg | 25.0 mg |
| Lactose | 65.0 mg | 148.4 mg |
| Corn Starch | 8.5 mg | 20.0 mg |
| Polyvinylpyrrolidone | 0.7 mg | 2.4 mg |
| Silicium dioxide (colloidal) | 0.3 mg | 1.2 mg |
| Magnesium stearate | 0.5 mg | 3.0 mg |

These tablets, which are provided with a second line can be administered orally in a dosage of one tablet two to four times per day.

Capsules may contain the active agent alone or admixed with an inert solid diluent, for example as mentioned above.

Capsules containing the ingredients indicated below may be prepared by conventional techniques and are administered at a dose of one capsule 2 to 4 times a day:

| Ingredient | Weight (mg) |
| --- | --- |
| Compound of formula I e.g. THIP | 5 |
| Inert solid diluent (starch, kaolin, calcium phosphate or carbonate, | |

| Ingredient | Weight (mg) |
| --- | --- |
| lactose, etc.) | 290 |

Solutions, suspensions, emulsions, dispersions, syrups and elixirs may contain the compound of formula I as the active agent in admixture with any of the conventional excipients utilized for the preparation of such compositions, e.g. suspending agents (methylcellulose, tragacanth and sodium alginate), wetting agents (lecithin, polyoxyethylene stearate and polyoxyethylene sorbitan monoleate), flavouring, colouring and sweetening agents and preservatives (ethyl-p-hydroxybenzoate).

Such liquid preparations may be put up in the form of e.g. injectable or oral liquid suspensions containing e.g 5 and 10 mg active ingredient respectively and suitable for administration once or 2 to 4 times per day.

I claim:

1. A method of alleviating pain in a subject in need of such treatment which method comprises administering to said subject an analgesically effective amount of 4,5,6,7-tetrahydroisoxazolo[5,4-c]-pyridine-3-ol.

2. A method according to claim 1 wherein 4,5,6,7-tetrahydroisoxazolo [5,4-c]-pyridin3-ol is administered at a daily dosage of from about 10 to about 200 mg.

3. A method according to claim 1 wherein 4,5,6,7-tetrahydroisoxazolo[5,4-c]-pyridin-3-ol is administered at a daily dosage of from about 15 to 100 mg.

4. A method according to claim 1 wherein 4,5,6,7-tetrahydroisoxazolo[5,4-c]-pyridin-3--ol is administered at a daily dosage of from about 20 to 50 mg.

5. A method according to claim 1 wherein 4,5,6,7-tetrahydroisoxazolo[5,4-c]-pyridin-3-ol is administered orally in unit dosage form.

* * * * *

UNITED STATES PATENT AND TRADEMARK OFFICE
CERTIFICATE OF CORRECTION

PATENT NO. : 4,315,934

DATED : February 16, 1982

INVENTOR(S) : Anne V. Christensen

It is certified that error appears in the above-identified patent and that said Letters Patent is hereby corrected as shown below:

Title page, Item [73]; delete "Sandoz Ltd., Basel, Switzerland" and substitute therefor -- H. Lundbeck & Co. A/S, København-Valby, Denmark --.

Signed and Sealed this

Fifth Day of August 1986

[SEAL]

Attest:

DONALD J. QUIGG

Attesting Officer

Commissioner of Patents and Trademarks